(12) United States Patent
Rindfleish

(10) Patent No.: US 6,672,311 B2
(45) Date of Patent: Jan. 6, 2004

(54) COLONOSCOPY PRESSURE DEVICE

(76) Inventor: Burton Rindfleish, 18 Longvue Ave., New Rochelle, NY (US) 10804

( * ) Notice: Subject to any disclaimer, the term of this patent is extended or adjusted under 35 U.S.C. 154(b) by 0 days.

(21) Appl. No.: 09/780,740

(22) Filed: Feb. 9, 2001

(65) Prior Publication Data

US 2002/0108617 A1 Aug. 15, 2002

(51) Int. Cl.[7] ................................................. A61F 5/37
(52) U.S. Cl. ........................... 128/874; 128/DIG. 20; 602/13; 602/19
(58) Field of Search .................. 602/5, 13; 128/845, 128/846, DIG. 20; 2/102, 108; 450/1

(56) References Cited

U.S. PATENT DOCUMENTS

| | | | |
|---|---|---|---|
| 1,589,670 A | * 6/1926 | Vartia | 602/13 |
| 3,521,623 A | * 7/1970 | Nichols | 602/13 |
| 4,120,297 A | 10/1978 | Rabischong et al. | |
| 4,178,923 A | * 12/1979 | Curlee | 128/DIG. 20 |
| 4,455,685 A | * 6/1984 | Steffler et al. | 2/2.1 A |
| 4,559,933 A | 12/1985 | Batard et al. | |
| 4,682,588 A | 7/1987 | Curlee | |
| 5,257,956 A | * 11/1993 | Ewen | 602/13 |
| 5,391,141 A | 2/1995 | Hamilton | |
| RE34,883 E | * 3/1995 | Grim | 602/13 |
| 5,685,321 A | 11/1997 | Klingenstein | |
| 5,728,055 A | 3/1998 | Sebastian | |

* cited by examiner

Primary Examiner—Michael A. Brown
(74) Attorney, Agent, or Firm—Furgang & Adwar, LLP

(57) ABSTRACT

This device is used for compressing the abdominal wall and colon during colonoscopy so as to facilitate the colonoscopy exam.

A vest including inflatable bladders is wrapped around a patient. The bladders are inflated to apply pressure to the patient's abdomen. Particularly, the bladders may apply pressure to the sigmoid, descending and ascending the colon of the patient to aid in a colonoscopy. The bladders may be selectively inflated, and deflated, in order to apply any desired amount of pressure to aid the doctor performing a colonoscopy examination. The bladders are enclosed between two layers of plastic to form the vest. The vest is inserted into a pillowcase-type slip, which is disposable. The vest is secured about the patient by such conventional connectors as hook and loop fasteners, located at the opposing ends of the vest.

24 Claims, 2 Drawing Sheets

COLONOSCOPY PRESSURE DEVICE

FIELD OF THE INVENTION

A device for compressing the abdominal wall and colon to facilitate a colonoscopy.

BACKGROUND OF THE INVENTION

Examination of the colon is performed for a variety of medical conditions. The colonoscope, inserted into a patient's rectum, contains a fiberoptic imaging device to provide a view of the colon and to assist in making a diagnosis. In addition to an imaging device, the probe may include a device to perform a procedure such as removing growths, such as polyps.

It is often difficult to advance the colonoscope through the entire length of a colon. Portions of the colon may become distended during the insertion of the colonoscope. The imaging device on the end of the probe may remain stationary or move backwards if this condition is encountered. This is a particular problem because portions of the colon, such as the sigmoid colon, are not fixed within the abdominal cavity. To combat this problem, it is common for a nurse or endoscopy assistant to manually compress the abdomen during the colonoscope insertion. External pressure is applied in an effort to support and move the colon. The application of external pressure helps advance the colonoscope by inhibiting the distension of the colon. However, it is common that the assistant not be able to sustain the correct amount of pressure or in the correct area. The inaccuracy and inadequacy of the application of pressure can result in the difficulty in advancing the colonoscope through the entire colon.

U.S. Pat. No. 5,685,321 (Klingenstein) discloses a device and method to facilitate a colonoscopy by externally compressing the colon. The device is a wrap that surrounds a patient's abdomen and has an inflatable bladder to apply force to the patient's abdomen. The inflatable bladder is placed on the wrap so that it covers the lower left-hand quadrant of the patient's abdomen. This placement allows the sigmoid colon to be supported. The bladder may have an additional flap of material stitched to the wrap or may be coupled to the wrap using hook and loop fasteners. The bladder can be repositioned on the belt. The bladder can have a variety of shapes to apply different compressive forces.

U.S. Pat. No. 4,120,297 (Rabischong et al.) discloses an orthopedic corset for correcting deformations or malformations of the spine. The corset has an inflatable bag enclosed in a fabric envelope.

U.S. Pat. No. 5,391,141 (Hamilton) discloses a device for applying pressure to a patient after body surgery. The device is an air bladder placed over the surgical wound. A vest is positioned directly over the air cushion and retains the cushion in place.

SUMMARY OF THE INVENTION

It is a primary object of the invention to provide a device for applying pressure to a patient's abdomen comprising a vest for encircling a patient's abdomen having two ends, a centerline of the vest located equidistant from each end, at least one pair of inflatable bladders retained by the vest, one bladder of the pair located on each side of the centerline.

It is another object of the invention to provide a vest for applying pressure to a patent's abdomen, comprising an inner layer and an outer layer, the inner and outer layers joined to one another and having a left side and right side and a centerline equidistant from the left and right sides, inflatable bladders located between the inner and outer layers for applying pressure when inflated, the inflatable bladders comprising at least a first and second bladder, the first and second bladder located equidistant from either side of the centerline.

It is another object of the invention to provide a method for applying pressure to a patient's abdomen comprising securing a vest about the patient, the vest having a pair of inflatable bladders, aligning the vest on the patient to have the bladders equally distanced from the centerline of the patient's abdomen, and inflating the bladders to apply pressure to the patient's abdomen.

It is yet another object of the invention to provide a method for performing a colonoscopy comprising securing a vest about the patient, the vest having a pair of inflatable bladders, aligning the vest on the patient to have the bladders equally distanced from the centerline of the patient's abdomen, inflating the bladders to apply pressure to the patient's abdomen and compressing the colon, while inserting the colonoscope.

It is an object of the invention to provide a vest that uses inflatable bladders to apply pressure to a patient's abdomen.

It is another object of the invention to provide a vest that applies pressure to a patient's abdomen to compress the patient's colon.

It is another object of the invention to provide a vest that has adjustable pressure applied against the abdomen.

It is yet another object of the invention to provide a belt that is adjustable in girth to fit a patient.

It is another object of the invention to provide a vest that applies pressure to cover the entire colon of the patient.

These and other objects of the invention will become apparent after reading the description of the invention that follows.

In one aspect of this invention of a device for applying pressure to a patient's abdomen, there is provided a vest for encircling a patient having two ends, a centerline of the vest located equidistant from each end. There is also provided at least one pair of inflatable bladders retained by the vest, one bladder of the pair located on each side of the centerline.

In yet another aspect of this invention of a vest for applying pressure to a patient's abdomen, the vest is provided an inner layer and an outer layer, the inner and outer layers joined to one another and having a left side and right side and a centerline equidistant from the left and right sides. Inflatable bladders are also provided and located between the inner and outer layers for applying pressure when inflated. The inflatable bladders comprise at least a first and second bladder, The first and second bladder located equidistant from either side of the centerline.

In yet another aspect of this invention a unique method for applying pressure to a patient's abdomen is provided. The method comprises the steps of (1) securing a vest about the patient, the vest having a pair of inflatable bladders; (2) then aligning the vest on the patient to have the bladders equally distanced from the centerline of the patient's abdomen; and (3) then inflating the bladders to apply pressure to the patient's abdomen.

DETAILED DESCRIPTION OF THE INVENTION

Figure 1:
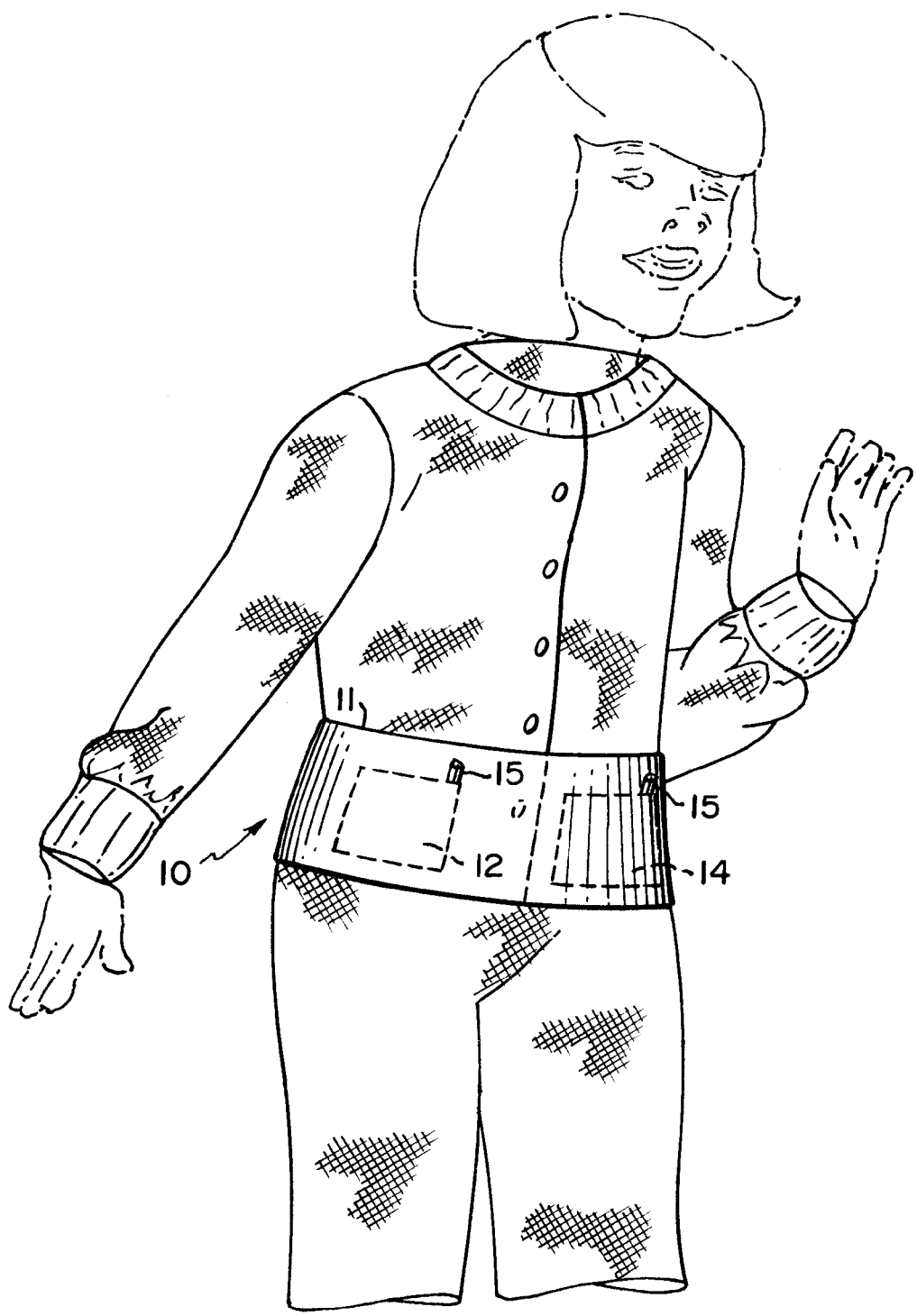
FIG. 1 is a view of the device in use on a patient.

The colonoscopy pressure device 10 is a vest that wraps around the patient. The device 10, as used on a patient, is shown in FIG. 1. The two ends 24, 26 of the vest 11 may be connected to each other to secure the vest 11 about the patient by any known means. Once connected, the vest 11 is tight about the patient. The vest 11 may have rectangular, inflatable bladders 12, 13 that may be selectively inflated and deflated. The bladders 12, 13 may be formed by heat welding two layers 42, 44 of the vest 11 to one another. Also, the bladders 12, 13 may be separately formed and attached to the vest 11 by any other means such as by being stitched into pockets (not shown). As the bladders 12, 13 are inflated, pressure is applied to the abdomen of the patient. Each bladder 12, 13 has a meter valve 15 to slowly reduce the pressure. Pressure maintains the position of the colon to facilitate passage of the colonoscope through the colon.

As the bladders 12, 13 are inflated, greater pressure is applied to the abdomen. The doctor can select the amount of pressure applied by varying the amount of inflation. The placement of the bladders 12, 13 insures the pressure is applied to the correct area of the abdomen. When the center of the vest 11 is aligned with the center of the abdomen, the bladders 12, 13 are in the correct position. The bladders 12, 13 may be separated by approximately one and one half inches on either side of the center of the abdomen to approximately four inches from the centerline as a function of the patient's waist. This is true regardless of the height of the person. The size of the bladders 12, 13 is large enough to cover the entire left and right side of the abdominal wall extending from the rib cage to the inguinal area. For a person 5'8" and above, the bladders 12, 13 may be approximately ten inches in height and approximately four to five inches in width. For an individual between the height of 5'4" and 5'8", each bladder may be approximately six inches in height and approximately three to four inches in width. For individuals 5' to 5'4" in height, the bladder size may be approximately five inches in height by approximately two inches in width.

Figure 2:
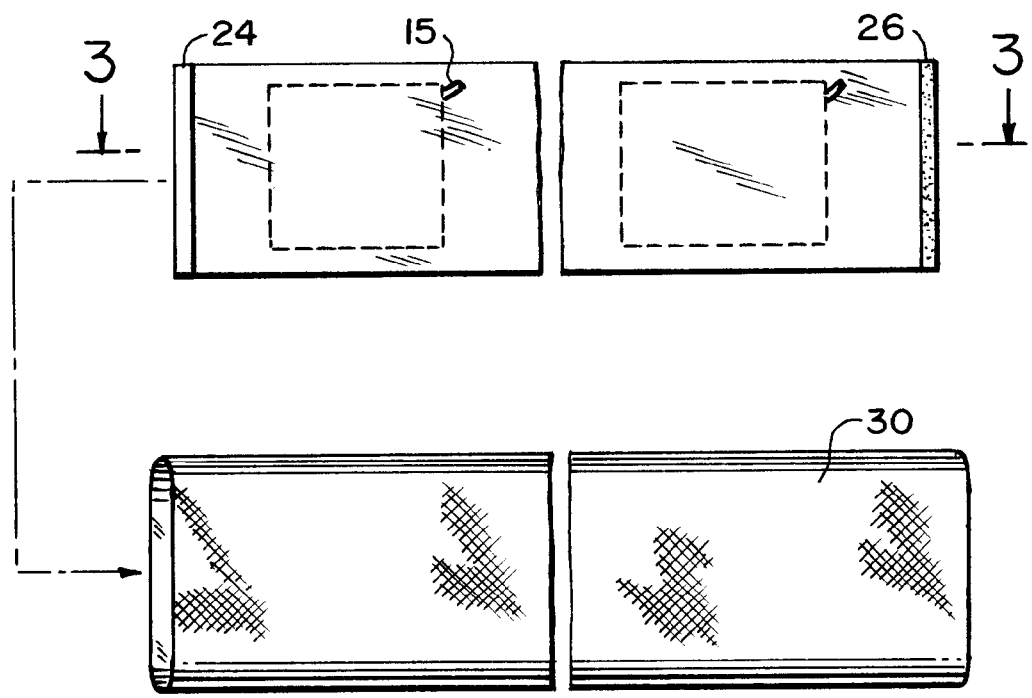
FIG. 2 is an exploded view of the device and slip.

As can be seen in FIG. 2, the vest 11 has a left and right end that are attached to one another about the individual. The two ends may be attached to one another in the posterior or anterior midline. The attachment has to be strong enough so that the vest 11 does not pull apart when the bladders 12, 13 are pressurized. Many conventional connectors, such as hook and loop fasteners 24, 26 (VELCRO®) are sufficient for this function. The device 10 may be placed within a pillowcase-type slip 30 which may be constructed of any well-known material, such as a soft fabric, for the comfort of the patient. Alternatively, the case may be a disposable plastic sheath. The slip may be disposable for sterile purposes.

Figure 3:
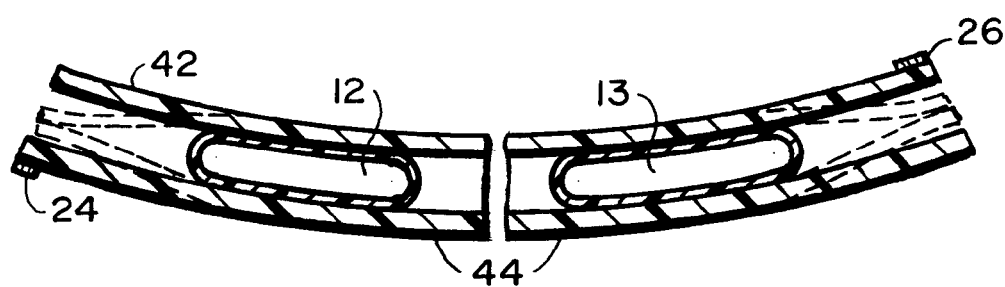
FIG. 3 is a cross-section of the vest about a patient (shown in phantom).

The structure of the vest 11 is seen by the depiction in FIG. 3. The vest 11 may be formed of any suitable material by two layers of plastic 42 and 44. The two layers 42, 44 of plastic are joined to one another to form the vest and the bladders 12, 13 are enclosed between the two inner layers 42, 44. The bladders 12, 13 can be inflated by any conventional means, such as hand operated pressure bulbs or a foot operated pump (not shown).

Many alternatives of the invention are possible. For instance, the two ends 24, 26 of the vest 11 can be connected by laces (not shown). In this instance, the laces extend to join or lace together the ends 24, 26. As the laces are tightened, the two ends 24, 26 draw closer to one another to secure the vest 11 about the patient. Also, the device 10 may be a Mae West, but instead of pockets with kapok, there are the inflatable bladders.

While the invention has been described with reference to a preferred embodiment, many modifications and variations would be known to one of ordinary skill in the art without departing from the scope of the invention. The description of the preferred embodiment is not intended to be limiting in any way, but the invention is defined by the appended claims.

What is claimed is:

1. A vest for applying pressure to a patient's abdomen, comprising:

an inner layer and an outer layer, said inner and outer layers joined to one another and having a left side and right side and a centerline equidistant from said left and right sides; and inflatable bladders located between said inner and outer layers for applying pressure when inflated, said inflatable bladders comprising at least a first and second bladder, said first and second bladder located equidistant from either side of said centerline.

2. The vest of claim 1, wherein said bladders are secured between said inner and outer layers.

3. The vest of claim 1, wherein each said inner and outer layer of said vest are heat sealed to one another.

4. The vest of claim 1, further comprising means for attaching said left and right sides of said vest together.

5. The vest of claim 1, further comprising a cover for encircling said vest.

6. The vest of claim 5, wherein said cover is removable.

7. The vest of claim 5, wherein said cover is made of fabric.

8. The vest of claim 5, wherein said inner and outer layer of said vest are plastic or fabric.

9. The vest of claim 1, wherein each said bladder is approximately ten inches in height and approximately four to five inches in width.

10. The device of claim 1, wherein each bladder is six inches in height and three to four inches in width.

11. The device of claim 1, wherein each bladder is five inches in height and two inches in width.

12. A method for performing a colonoscopy of the type wherein a vest is provided comprising:

a) providing a pair of inflatable bladders;

b) attaching the bladders to the vest;

c) securing the vest about a patient's waist;

b) aligning the vest on the patient so that the bladders equally distanced from the centerline of the patient's abdomen; and c) inflating the bladders selectively to compress the colon.

13. The method of claim 12, further comprising the step of inserting a colonoscope in the patient.

14. The method of claim 12, further comprising the step of inflating at least one bladder with a hand bulb or foot pump.

15. A device for applying pressure to a patient's abdomen comprising:

a vest for encircling a patient having two ends, a top edge and a bottom edge, and a centerline of the vest located equidistant from each end;

the vest having a substantially constant height; and formed by two flexible layers joined at their edges, and at least one pair of inflatable bladders retained by the vest, at least one said bladder is located between said two layer and one bladder of the pair located on each side of said centerline.

16. A device for applying pressure to a patient's abdomen comprising:

a vest for encircling a patient having two ends, a top edge and a bottom edge, and a centerline of the vest located equidistant from each end;

the vest having a substantially constant height; and at least one pair of inflatable bladders retained by the vest, one bladder of the pair located on each side of said centerline and spaced from said centerline in a range of one and one half inches to four from said centerline.

17. A device for applying pressure to a patient's abdomen comprising:

a vest for encircling a patient having two ends, a top edge and a bottom edge, and a centerline of the vest located equidistant from each end;

the vest having a substantially constant height; and at least one pair of inflatable bladders retained by the vest, one bladder of the pair located on each side of said centerline, and each said bladder is approximately ten inches in height and approximately four to five inches in width.

18. A device for applying pressure to a patient's abdomen comprising:

a vest for encircling a patient having two ends, a top edge and a bottom edge, and a centerline of the vest located equidistant from each end;

the vest having a substantially constant height; and at least one pair of inflatable bladders retained by the vest, one bladder of the pair located on each side of said centerline and each said bladder is approximately six inches in height and approximately three to four inches in width.

19. A device for applying pressure to a patient's abdomen comprising:

a vest for encircling a patient having two ends, a top edge and a bottom edge, and a centerline of the vest located equidistant from each end;

the vest having a substantially constant height; and at least one pair of inflatable bladders retained by the vest, one bladder of the pair located on each side of said centerline and each said bladder is approximately five inches in height and approximately two inches in width.

20. A device for applying pressure to a patient's abdomen comprising:

a vest for encircling a patient having two ends, a centerline of the vest located equidistant from each end and said vest is formed by two flexible layers joined at their edges, at least one of said bladders is located between said two layers; and at least one pair of inflatable bladders retained by the vest, one bladder of the pair located on each side of said centerline; and means for selectively varying the pressure in the bladders.

21. A device for applying pressure to a patient's abdomen comprising:

a vest for encircling a patient having two ends, a centerline of the vest located equidistant from each end; and at least one pair of inflatable bladders retained by the vest, one bladder of the pair located on each side of said centerline and spaced from said centerline in a range of one and one half inches to four from said centerline; and means for selectively varying the pressure in the bladders.

22. A device for applying pressure to a patient's abdomen comprising:

a vest for encircling a patient having two ends, a centerline of the vest located equidistant from each end; and at least one pair of inflatable bladders retained by the vest, one bladder of the pair located on each side of said centerline and each said bladder is approximately ten inches in height and approximately four to five inches in width; and means for selectively varying the pressure in the bladders.

23. A device for applying pressure to a patient's abdomen comprising:

a vest for encircling a patient having two ends, a centerline of the vest located equidistant from each end; and at least one pair of inflatable bladders retained by the vest, one bladder of the pair located on each side of said centerline and each said bladder is approximately six inches in height and approximately three to four inches in width; and means for selectively varying the pressure in the bladders.

24. A device for applying pressure to a patient's abdomen comprising:

a vest for encircling a patient having two ends, a centerline of the vest located equidistant from each end; and at least one pair of inflatable bladders retained by the vest, one bladder of the pair located on each side of said centerline and each said bladder is approximately five inches in height and approximately two inches in width; and means for selectively varying the pressure in the bladders.

* * * * *